United States Patent

Kudis et al.

(10) Patent No.: US 6,667,333 B2
(45) Date of Patent: Dec. 23, 2003

(54) HERBICIDAL 3-(4,5 DIHYDROISOXAZOLE-3 YL) SUBSTITUTED BENZOYCYCLOHEXENONE DERIVATIVES

(75) Inventors: Steffen Kudis, Mannheim (DE); Ernst Baumann, Dudenhofen (DE); Wolfgang von Deyn, Neustadt (DE); Klaus Langemann, Worms (DE); Guido Mayer, Neustadt (DE); Ulf Misslitz, Neustadt (DE); Ulf Neidlein, Mannheim (DE); Matthias Witschel, Bad Dürkheim (DE); Karl-Otto Westphalen, Speyer (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/130,021
(22) PCT Filed: Nov. 29, 2000
(86) PCT No.: PCT/EP00/11907
  § 371 (c)(1),
  (2), (4) Date: May 13, 2002
(87) PCT Pub. No.: WO01/40200
  PCT Pub. Date: Jun. 7, 2001

(65) Prior Publication Data
US 2003/0092576 A1 May 15, 2003

(30) Foreign Application Priority Data
Dec. 2, 1999 (DE) .......................... 199 58 033

(51) Int. Cl.⁷ ...................... A10N 43/80; A61K 31/423; C07D 261/20; C07D 498/00
(52) U.S. Cl. .................. 514/379; 504/271; 548/241
(58) Field of Search .................. 548/241; 514/379; 504/271

(56) References Cited

U.S. PATENT DOCUMENTS 6,004,903 A  12/1999 von Deyn et al.

FOREIGN PATENT DOCUMENTS

WO  96/26200  8/1996

*Primary Examiner*—Taofiq Solola
(74) *Attorney, Agent, or Firm*—Keil & Weinkauf

(57) ABSTRACT

3-(4,5-Dihydroisoxazol-3-yl)-substituted benzoylcyclohexenone derivatives of the formula I

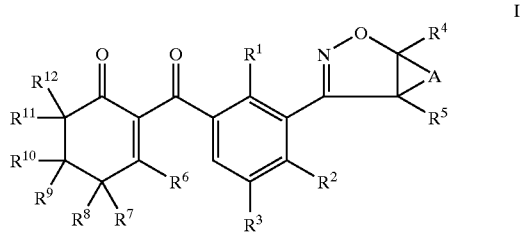

in which the substituents A and $R^1$ to $R^{12}$ are as defined in the description and their agriculturally useful salts are described. The compounds have herbicidal action.

14 Claims, No Drawings

HERBICIDAL 3-(4,5 DIHYDROISOXAZOLE-3 YL) SUBSTITUTED BENZOYCYCLOHEXENONE DERIVATIVES

This application is a 371 of PCT/EP00/11907 filed Nov. 29, 2000.

FIELD OF INVENTION

The present invention relates to certain 3-(4,5-dihydroisoxazol-3-yl)-substituted benzoylcyclohexenone derivatives and to processes for their preparation, to compositions comprising them and to the use of these derivatives or of the compositions comprising them for controlling harmful plants.

BACKGROUND INFORMATION

WO 96/26200 discloses herbicidal 2-benzoylcyclohexane-1,3-diones.

However, the herbicidal properties of the prior-art compounds and their compatibility with crop plants are not entirely satisfactory. It is an object of the present invention to provide novel, in particular herbicidally active, compounds having improved properties.

BRIEF SUMMARY

We have found that this object is achieved by the 3-(4,5-dihydroisoxazol-3-yl)-substituted benzoylcyclohexenone derivatives of the formula I

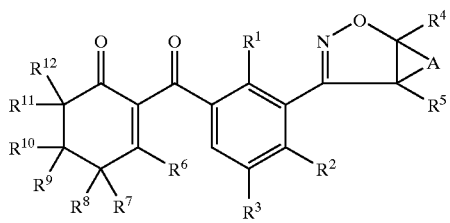

in which

A is $C_1$–$C_4$-alkanediyl which may carry one, two or three substituents selected from the group consisting of halogen and $C_1$–$C_4$-alkyl;

$R^1$ is $C_1$–$C_6$-alkyl, $C_1$–$C_6$-haloalkyl, $C_1$–$C_6$-alkoxy, $C_1$–$C_6$-haloalkoxy, halogen or nitro;

$R^2$ is $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, cyano, halogen or nitro;

$R^3$ is hydrogen, $C_1$–$C_6$-alkyl or halogen;

$R^4$, $R^5$ independently of one another are hydrogen, $C_1$–$C_4$-alkyl or $C_1$–$C_4$-haloalkyl; or $R^4$, $R^5$ together are $C_1$–$C_4$-alkanediyl which may carry one, two or three substituents selected from the group consisting of halogen and $C_1$–$C_4$-alkyl;

$R^6$ is hydroxyl, mercapto, halogen, $OR^{13}$, $SOR^{14}$, $SR^{13}$ or $SO_2R^{14}$;

$R^7$, $R^{11}$ independently of one another are hydrogen, $C_1$–$C_4$-alkyl, $C_1$–$C_4$-alkylthio or $C_1$–$C_4$-alkoxycarbonyl;

$R^8$, $R^{10}$, $R^{12}$ independently of one another are hydrogen or $C_1$–$C_4$-alkyl;

$R^9$ is hydrogen, hydroxyl, halogen, $C_1$–$C_6$-alkyl, $C_1$–$C_6$-haloalkyl, di($C_1$–$C_6$-alkoxy)methyl, ($C_1$–$C_6$-alkoxy)($C_1$–$C_6$-alkylthio)methyl, di($C_1$–$C_6$-alkylthio)methyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkoxycarbonyl, $C_1$–$C_6$-haloalkoxycarbonyl, 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the six last mentioned radicals may carry one, two or three substituents selected from $C_1$–$C_4$-alkyl; or $R^7$ and $R^8$ or $R^{11}$ and $R^{12}$ together are $C_1$–$C_5$-alkanediyl which may carry one, two or three substituents selected from the group consisting of halogen, cyano, $C_1$–$C_4$-alkyl, $C_1$–$C_4$-haloalkyl and $C_1$–$C_4$-alkoxycarbonyl; or $R^8$ and $R^9$ or $R^9$ and $R^{12}$ together are a chemical bond or $C_1$–$C_5$-alkanediyl which may carry one, two or three substituents selected from the group consisting of halogen, cyano, $C_1$–$C_4$-alkyl, $C_1$–$C_4$-haloalkyl and $C_1$–$C_4$-alkoxycarbonyl; or $R^8$ and $R^{12}$ together are $C_1$–$C_4$-alkanediyl which may carry one, two or three substituents selected from the group consisting of halogen, cyano, $C_1$–$C_4$-alkyl, $C_1$–$C_4$-alkoxycarbonyl; or $R^9$ and $R^{10}$ together are —O—$(CH_2)_p$—O—, —O—$(CH_2)_p$—S—, —S—$(CH_2)_p$—S—, —O—$(CH_2)_q$— or —S—$(CH_2)_q$— which may carry one, two or three substituents selected from the group consisting of halogen, cyano, $C_1$–$C_4$-alkyl, $C_1$–$C_4$-haloalkyl and $C_1$–$C_4$-alkoxycarbonyl; or $R^9$ and $R^{10}$ together are an oxygen atom;

$R^{13}$ is $C_1$–$C_6$-alkyl, $C_3$–$C_6$-alkenyl, $C_3$–$C_6$-haloalkenyl, $C_3$–$C_6$-alkynyl, $C_3$–$C_6$-cycloalkyl, $C_1$–$C_{20}$-alkylcarbonyl, $C_2$–$C_{20}$-alkenylcarbonyl, $C_2$–$C_6$-alkynylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N,N-di($C_1$–$C_6$-alkyl)aminothiocarbonyl, $C_1$–$C_6$-alkoxyimino–$C_1$–$C_6$-alkyl, where the alkyl, alkoxy and cycloalkyl radicals mentioned may be partially or fully halogenated and/or may carry one, two or three substituents selected from the group consisting of cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-($C_1$–$C_4$-alkoxycarbonyl, $C_1$–$C_4$-alkylaminocarbonyl, N,N-di-($C_1$–$C_4$-alkyl)aminocarbonyl or $C_3$–$C_6$-cycloalkyl;

is phenyl, phenyl-$C_1$–$C_6$-alkyl, phenylcarbonyl-$C_1$–$C_6$-alkyl, phenylcarbonyl, phenoxycarbonyl, phenoxythiocarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl, where the phenyl or heterocyclyl radical of the radicals mentioned may be partially or fully halogenated and/or may carry one, two or three substituents selected from the group consisting of nitro, cyano, $C_1$–$C_4$-alkyl, $C_1$–$C_4$-haloalkyl, $C_1$–$C_4$-alkoxy and $C_1$–$C_4$-haloalkoxy;

$R^{14}$ is $C_1$–$C_6$-alkyl, $C_3$–$C_6$-alkenyl, $C_3$–$C_6$-haloalkenyl, $C_3$–$C_6$-alkynyl or $C_3$–$C_6$-cycloalkyl, where the alkyl and cycloalkyl radicals mentioned may be partially or fully halogenated and/or may carry one, two or three substituents selected from the group consisting of cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, $C_1$–$C_4$-alkylaminocarbonyl, N,N-di($C_1$–$C_4$-alkyl)aminocarbonyl or $C_3$–$C_6$-cycloalkyl;

is phenyl, phenyl-$C_1$–$C_6$-alkyl, phenylcarbonyl-$C_1$–$C_6$-alkyl, heterocycyl, heterocyclyl-$C_1$–$C_6$-alkyl or heterocyclylcarbonyl-$C_1$–$C_6$-alkyl, where the phenyl or heterocyclyl radical of the radicals mentioned may be partially or fully halogenated and/or may carry one, two or three substituents selected the group consisting of nitro, cyano, $C_1$–$C_4$-alkyl, $C_1$–$C_4$-haloalkyl, $C_1$–$C_4$-alkoxy and $C_1$–$C_4$-haloalkoxy;

p is 2, 3 or 4;

q is 1, 2, 3, 4 or 5;

and their agriculturally useful salts.

Furthermore, we have found herbicidal compositions which comprise the compounds I and have very good herbicidal activity. Moreover, we have found processes for preparing these compositions and methods for controlling undesirable vegetation using the compounds I.

DETAILED DESCRIPTION OF THE INVENTION

Depending on the substitution pattern, the compounds of the formula I may contain one or more centers of chirality, in which case they are present as enantiomer or diastereomer mixtures. The invention provides both the pure enantiomers or diastereomers and their mixtures. The compounds of the formula I where $R^6$=OH or SH can also be present as tautomers of the structure shown, or as tautomer mixtures.

The compounds of the formula I may also be present in the form of their agriculturally useful salts, the nature of the salt generally being immaterial. In general, the salts of those cations and the acid addition salts of those acids are suitable whose cations and anions, respectively, do not adversely affect the herbicidal action of compounds I.

Suitable cations are, in particular, ions of the alkali metals, preferably lithium, sodium and potassium, the alkaline earth metals, preferably calcium and magnesium, and the transition metals, preferably manganese, copper, zinc and iron, and also ammonium where, if desired, one to four hydrogens may be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri($C_1$–$C_4$-alkyl)sulfonium, and sulfoxonium ions, preferably tri($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate.

The organic moieties mentioned for the substituents $R^1$–$R^{14}$ or as radicals on phenyl rings are collective terms for individual enumerations of the individual group members. All hydrocarbon chains, i.e. alkyl, haloalkyl, dialkoxymethyl, alkoxyalkylthiomethyl, dialkylthiomethyl, alkoxy, haloalkoxy, alkylthio, haloalkylthio, alkylsulfinyl,

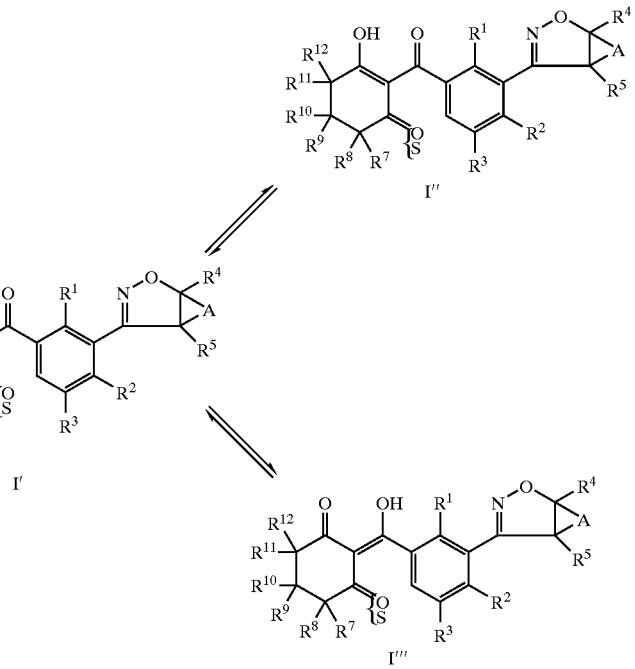

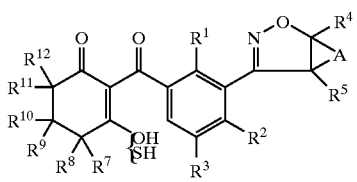

I where $R^6$ = OH, SH haloalkylsulfinyl, alkylsulfonyl, haloalkylsulfonyl, dialkylamino, alkylcarbonyl, alkoxycarbonyl, haloalkoxycarbonyl, alkylthiocarbonyl, alkoxyalkoxycarbonyl, alkylaminocarbonyl, dialkylaminocarbonyl, dialkylaminothiocarbonyl, alkoxyiminoalkyl, N-alkoxy-N-alkylaminocarbonyl, phenylalkyl, heterocyclylalkyl, phenylcarbonylalkyl, heterocyclylcarbonylalkyl, alkenylcarbonyl, alkenyloxycarbonyl, alkenylaminocarbonyl, N-alkenyl-N-alkylaminocarbonyl, alkynylcarbonyl, alkynyloxycarbonyl, alkynylaminocarbonyl, N-alkynyl-N-alkylaminocarbonyl, alkenyl, alkynyl, haloalkenyl moieties can be straight-chain or branched. Unless indicated otherwise, halogenated substituents preferably carry one to five identical or different halogen atoms. The term halogen denotes in each case fluorine, chlorine, bromine or iodine.

Examples of other meanings are:

$C_1$–$C_4$-alkyl, and the alkyl moieties of $C_1$–$C_4$-alkylcarbonyl, phenyl-$C_1$–$C_4$-alkyl, phenylcarbonyl-$C_1$–$C_4$-alkyl, heterocyclyl-$C_1$–$C_4$-alkyl and heterocyclylcarbonyl-$C_1$–$C_4$-alkyl: for example methyl, ethyl, propyl, 1-methylethyl, butyl, 1-methylpropyl, 2-methylpropyl and 1,1-dimethylethyl;

$C_1$–$C_6$-alkyl, and the alkyl moieties of $C_1$–$C_6$-alkylcarbonyl-N—$C_3$–$C_6$-alkenyl-N—$C_1$–$C_6$-alkylaminocarbonyl, N—$C_3$–$C_6$-alkynyl-N—$C_1$–$C_6$-alkylaminocarbonyl, N—$C_1$–$C_6$-alkoxy-N—$C_1$–$C_6$-alkylaminocarbonyl, $C_1$–$C_6$-alkoxyimino-$C_1$–$C_6$-alkyl, phenyl-$C_1$–$C_6$-alkyl, phenylcarbonyl-$C_1$–$C_6$-alkyl, heterocyclyl-$C_1$–$C_6$-alkyl, heterocyclylcarbonyl-$C_1$–$C_6$-alkyl: $C_1$–$C_4$-alkyl as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_{20}$-alkyl as alkyl moiety of $C_1$–$C_{20}$-alkylcarbonyl: $C_1$–$C_6$-alkyl as mentioned above, and also heptyl, octyl, pentadecyl or heptadecyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, bromomethyl, iodomethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_6$-haloalkyl: $C_1$–$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-alkoxy and the alkoxy moieties of $C_1$–$C_4$-alkoxycarbonyl and $C_1$–$C_4$-alkoxy-$C_1$–$C_4$-alkoxycarbonyl: for example methoxy, ethoxy, propoxy, 1-methylethoxy, butoxy, 1-methylpropoxy, 2-methylpropoxy and 1,1-dimethylethoxy;

$C_1$–$C_6$-alkoxy, and the alkoxy moieties of $C_1$–$C_6$-alkoxycarbonyl, di($C_1$–$C_6$-alkoxy)methyl, ($C_1$–$C_6$-alkoxy)($C_1$–$C_6$-alkylthio)methyl, N-($C_1$–$C_6$-alkoxy)-N-($C_1$–$C_6$-alkyl)aminocarbonyl and $C_1$–$C_6$-alkoxyimino-$C_1$–$C_6$-alkyl: $C_1$–$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_6$-haloalkoxy, and the haloalkoxy moieties of $C_1$–$C_6$-haloalkoxycarbonyl: $C_1$–$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_4$-alkylthio: for example methylthio, ethylthio, propylthio, 1-methylethylthio, butylthio, 1-methylpropylthio, 2-methylpropylthio and 1,1-dimethylethylthio;

$C_1$–$C_6$-alkylthio, and the alkylthio radicals of ($C_1$–$C_6$-alkoxy)($C_1$–$C_6$-alkylthio)methyl, di($C_1$–$C_6$-alkylthio)methyl and ($C_1$–$C_6$-alkylthio)carbonyl: $C_1$–$C_4$-alkylthio, as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_4$-haloalkylthio: a $C_1$–$C_4$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio and nonafluorobutylthio;

$C_1$–$C_6$-haloalkylthio: $C_1$–$C_4$-haloalkylthio as mentioned above, and also, for example, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$–$C_6$-alkylsulfinyl ($C_1$–$C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl;

$C_1$–$C_6$-haloalkylsulfinyl: $C_1$–$C_6$-alkylsulfinyl radical as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl;

$C_1$–$C_4$-alkylsulfonyl ($C_1$–$C_4$-alkyl-S(=O)$_2$—), and the alkylsulfonyl moieties of $C_1$–$C_4$-alkylsulfonyloxy: for example methylsulfonyl, ethylsulfonyl, propylsulfonyl, 1-methylethylsulfonyl, butylsulfonyl, 1-methylpropylsulfonyl, 2-methylpropylsulfonyl and 1,1-Dimethylethylsulfonyl;

$C_1$–$C_6$-alkylsulfonyl: a $C_1$–$C_4$-alkylsulfonyl radical as mentioned above, and also, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_6$-haloalkylsulfonyl: a $C_1$–$C_6$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

di($C_1$–$C_4$-alkyl)amino, and the dialkylamino moieties of di($C_1$–$C_4$-alkyl)aminocarbonyl: N,N-dimethylamino, N,N-diethylamino, N,N-dipropylamino, N,N-di(1- methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$–$C_6$-alkylamino) as dialkylamino moiety of di($C_1$–$C_6$-alkyl)aminocarbonyl and di($C_1$–$C_6$-alkyl) aminothiocarbonyl: N-methyl-N-pentylamino or N-methyl-N-hexylamino;

($C_1$–$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

($C_1$–$C_6$-alkylamino)carbonyl: ($C_1$–$C_4$-alkylamino)carbonyl, as mentioned above, and also, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl;

$C_3$–$C_6$-alkenyl, and the alkenyl moieties of $C_3$–$C_6$-alkenylcarbonyl, $C_3$–$C_6$-alkenyloxycarbonyl, $C_3$–$C_6$-alkenylaminocarbonyl, N-($C_3$–$C_6$-alkenyl)-N-($C_1$–$C_6$-alkyl)aminocarbonyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_2$–$C_6$-alkenyl as alkenyl moiety of $C_2$–$C_6$-alkenylcarbonyl: $C_3$–$C_6$-alkenyl as mentioned above, and also ethenyl;

$C_2$–$C_{20}$-alkenyl as alkenyl moiety of $C_2$–$C_{20}$-alkenylcarbonyl: $C_2$–$C_6$-alkenyl as mentioned above and also 8-pentadecen-1-yl, 8-heptadecen-1-yl and 8,11-heptadecadien-1-yl;

$C_3$–$C_6$-haloalkenyl: a $C_3$–$C_6$-alkenyl radical as mentioned above which is partially or fully substituted by fluorine, chlorine, bromine and/or iodine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

$C_3$–$C_6$-alkynyl, and the alkynyl moieties of $C_3$–$C_6$-alkynylcarbonyl, $C_3$–$C_6$-alkynyloxycarbonyl, $C_3$–$C_6$-alkynylaminocarbonyl, N-($C_3$–$C_6$-alkynyl)-N-($C_1$–$C_6$-alkyl)aminocarbonyl: for example propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_2$–$C_6$-alkynyl as alkynyl moiety of $C_2$–$C_6$-alkynylcarbonyl: $C_3$–$C_6$-alkynyl, as mentioned above, and also ethynyl;

$C_1$–$C_4$-alkanediyl: for example methanediyl, ethane-1,2-diyl, propane-1,3-diyl or butane-1,4-diyl;

$C_1$–$C_5$-alkanediyl: $C_1$–$C_4$-alkanediyl as mentioned above, and also pentane-1,5-diyl;

$C_3$–$C_6$-cycloalkyl, and the cycloalkyl moieties of $C_3$–$C_6$-cycloalkylcarbonyl: for example cyclopropyl, cyclobutyl, cyclopentyl or cyclohexyl;

heterocyclyl, and heterocyclyl moieties of heterocyclylcarbonyl, heterocyclyl-$C_1$–$C_6$-alkyl, heterocyclyloxycarbonyl, heterocyclyloxythiocarbonyl, heterocyclylcarbonyl-$C_1$–$C_6$-alkyl: a saturated, partially saturated or unsaturated 5- or 6-membered heterocyclic ring which contains one to four identical or different hetero atoms selected from the following group: oxygen, sulfur or nitrogen, and can be bonded via C or N, i.e. for example, C-bonded 5-membered saturated rings such as:

tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bonded, 5-membered partially saturated rings such as: 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-Dithiol-4-yl, 1,3-oxathiol-2-yl, 1,3-oxathiol-4-yl, 1,3-oxathiol-5-yl, 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta^4$-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl;

C-bonded, 5-membered unsaturated rings such as: 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bonded, 6-membered saturated rings, such as: tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

C-bonded, 6-membered partially saturated rings such as: 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydropyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-thiazin-4-yl, 6H-1,3-thiazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

C-bonded, 6-membered unsaturated rings such as: pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bonded, 5-membered saturated rings such as: tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bonded, 5-membered partially saturated rings such as: 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-Thiadiazolin-2-yl, 1,2,4-$\Delta^3$-Thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl;

N-bonded, 5-membered unsaturated rings such as: pyrrol-1-yl, pyrazol-1-yl, imidazol-1-yl, 1,2,3-triazol-1-yl, 1,2,4-triazol-1-yl, tetrazol-1-yl;

N-bonded, 6-membered saturated rings such as: piperidin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl;

and N-bonded, 6-membered partially saturated rings such as: 1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6- tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

where, if appropriate, the sulfur of the heterocycles mentioned may be oxidized to S=O or S(=O)$_2$ and where a bicyclic ring system may be formed together with a fused phenyl ring or a $C_3$–$C_6$-carboxycycle or a further 5- to 6-membered heterocycle.

The phenyl rings or heterocyclyl radicals are preferably unsubstituted or carry one, two or three halogen atoms and/or one nitro group, one cyano group, one or two methyl, trifluoromethyl, methoxy or trifluoromethoxy groups.

In the formula I,

A is preferably methanediyl, propane-1,3-diyl or butane-1,4-diyl, each of which may carry one, two or three substituents selected from the group consisting of halogen and $C_1$–$C_4$-alkyl;
  in particular methanediyl, which is advantageously unsubstituted;

$R^1$ is preferably $C_1$–$C_6$-alkyl, $C_1$–$C_6$-haloalkyl, $C_1$–$C_6$-alkoxy or halogen;
  in particular $C_1$–$C_4$-alkyl, preferably methyl, ethyl, n-propyl or isopropyl; halogen, preferably fluorine, chlorine or bromine;
  particularly preferably methyl or chlorine;
  most preferably methyl;

$R^2$ is preferably $C_1$–$C_6$-haloalkyl, $C_1$–$C_6$-alkylsulfonyl, halogen or nitro; in particular $C_1$–$C_4$-haloalkyl, preferably difluoromethyl or trifluoromethyl; $C_1$–$C_4$-alkylsulfonyl, preferably methylsulfonyl or ethylsulfonyl; or halogen, preferably fluorine or chlorine;
  particularly preferably $C_1$–$C_4$-alkylsulfonyl, most preferably methylsulfonyl;

$R^3$ is preferably hydrogen, $C_1$–$C_4$-alkyl or halogen; in particular hydrogen, chlorine or methyl; particularly preferably hydrogen;

$R^4$ is preferably hydrogen, $C_1$–$C_4$-alkyl or $C_1$–$C_4$-haloalkyl; in particular hydrogen, methyl, ethyl, chloromethyl or bromomethyl; particularly preferably hydrogen or methyl;

$R^5$ is preferably hydrogen or $C_1$–$C_4$-alkyl; in particular hydrogen or methyl particularly preferably hydrogen; or $R^4$, $R^5$ together are preferably a $C_1$–$C_4$-alkanediyl group; in particular a methanediyl group;

$R^6$ is preferably hydroxyl, $OR^{13}$, $SR^{13}$, $SOR^{14}$ or $SO_2R^{14}$; in particular hydroxyl, $OR^{13}$ or $SR^{13}$; particularly preferably hydroxyl;

$R^7$, $R^{11}$ independently of one another are preferably hydrogen, $C_1$–$C_4$-alkyl or $C_1$–$C_4$-alkylthio; in particular hydrogen, methyl or methylthio; particularly preferably hydrogen;

$R^8$, $R^{10}$, $R^{12}$ independently of one another are preferably hydrogen or methyl;

$R^9$ is preferably hydrogen, hydroxyl, $C_1$–$C_6$-alkyl or di($C_1$–$C_6$-alkoxy)methyl; in particular hydrogen or $C_1$–$C_4$-alkyl;

or $R^7$ and $R^8$ or $R^8$ and $R^9$ or $R^9$ and $R^{12}$ or $R^8$ and $R^{12}$ or $R^{11}$ and $R^{12}$ together are preferably $C_1$–$C_5$-alkanediyl which may carry one, two or three substituents selected from the group consisting of halogen, cyano, $C_1$–$C_4$-alkyl, $C_1$–$C_4$-haloalkyl and $C_1$–$C_4$-alkoxycarbonyl;

or $R^9$ and $R^{10}$ together are preferably an oxygen atom;

$R^{13}$ is preferably $C_1$–$C_6$-alkyl, $C_1$–$C_{20}$-alkylcarbonyl, preferably $C_1$–$C_6$-alkylcarbonyl, $C_1$–$C_6$-alkoxycarbonyl, $C_1$–$C_6$-alkylthiocarbonyl, where the alkyl and alkoxy radicals mentioned may be partially or fully halogenated and/or may carry one, two or three substituents selected from the group consisting of cyano, $C_1$–$C_4$-alkoxy, $C_1$–$C_4$-alkylthio, $C_1$–$C_4$-alkylcarbonyl, $C_1$–$C_4$-alkoxycarbonyl and $C_3$–$C_6$-cycloalkyl is preferably phenyl, phenyl-$C_1$–$C_4$-alkyl, phenylcarbonyl-$C_1$–$C_4$-alkyl, phenylcarbonyl, phenoxycarbonyl, heterocyclyl, heterocyclyl-$C_1$–$C_4$-alkyl, heterocyclylcarbonyl-$C_1$–$C_4$-alkyl, heterocyclyloxycarbonyl, where the phenyl or heterocyclyl radical of the radicals mentioned may be partially or fully halogenated and/or may carry one, two or three substituents selected from the group consisting of nitro, cyano, $C_1$–$C_4$-alkyl, $C_1$–$C_4$-haloalkyl, $C_1$–$C_4$-alkoxy and $C_1$–$C_4$-haloalkoxy;

$R^{14}$ is preferably $C_1$–$C_6$-alkyl which may be partially or fully halogenated and/or may carry one, two or three substituents selected from the group consisting of cyano, $C_1$–$C_4$-alkoxy, $C_1$–$C_4$-alkylthio, $C_1$–$C_4$-alkylcarbonyl, $C_1$–$C_4$-alkoxycarbonyl and $C_3$–$C_6$-cycloalkyl; is preferably phenyl, phenyl-$C_1$–$C_4$-alkyl, phenylcarbonyl-$C_1$–$C_4$-alkyl, heterocyclyl, heterocyclyl-$C_1$–$C_4$-alkyl or heterocyclyl-carbonyl-$C_1$–$C_4$-alkyl, where the phenyl or heterocyclyl radical of the radicals mentioned may be partially or fully halogenated and/or may carry one, two or three substituents selected from the group consisting of nitro, cyano, $C_1$–$C_4$-alkyl, $C_1$–$C_4$-haloalkyl, $C_1$–$C_4$-alkoxy and $C_1$–$C_4$-haloalkoxy.

Particular preference is given to 3-(4,5-dihydroisoxazol-3-yl) substituted benzoylcyclohexanone derivatives of the formula I in which A is methanediyl.

Particular preference is given to 3-(4,5-dihydroisoxazol-3-yl) substituted benzoylcyclohexanone derivatives of the formula I in which $R^1$ is $C_1$–$C_4$-alkyl or halogen;
$R^2$ is $C_1$–$C_4$-haloalkyl, $C_1$–$C_4$-alkylsulfonyl or halogen;
$R^3$ is hydrogen;
$R^4$ is hydrogen, $C_1$–$C_4$-alkyl or $C_1$–$C_4$-haloalkyl;
$R^5$ is hydrogen or $C_1$–$C_4$-alkyl.

Particular preference is furthermore given to 3-(4,5-dihydroisoxazol-3-yl) substituted benzoylcyclohexanone derivatives of the formula I in which $R^7$ and $R^{11}$ independently of one another are hydrogen, $C_1$–$C_4$-alkyl or $C_1$–$C_4$-alkylthio;
$R^8$, $R^{10}$, $R^{12}$ independently of one another are hydrogen or methyl and
$R^9$ is hydrogen, hydroxyl, $C_1$–$C_6$-alkyl or di($C_1$–$C_6$-alkoxy)methyl; or
$R^7$ and $R^8$ or $R^8$ and $R^9$ or $R^9$ and $R^{12}$ or $R^8$ and $R^{12}$ or $R^{11}$ and $R^{12}$ together are $C_1$–$C_5$-alkanediyl which may carry one, two or three substituents selected from the group consisting of halogen, cyano, $C_1$–$C_4$-alkyl, $C_1$–$C_4$-haloalkyl and $C_1$–$C_4$-alkoxycarbonyl or
$R^9$ and $R^{10}$ together are an oxygen atom.

Particular preference is furthermore given to 3-(4,5-dihydroisoxazol-3-yl) substituted benzoylcyclohexanone derivatives of the formula I in which $R^6$ is hydroxyl, $OR^{13}$ or $SR^{13}$; and $R^{13}$ is $C_1$–$C_6$-alkyl, $C_1$–$C_{20}$-alkylcarbonyl, $C_1$–$C_6$-alkoxycarbonyl, $C_1$–$C_6$-alkylthiocarbonyl, where the alkyl and alkoxy radicals may be partially or fully halogenated and/or may carry one, two or three substituents selected from the group consisting of cyano, $C_1$–$C_4$-alkoxy, $C_1$–$C_4$-alkylthio, $C_1$–$C_4$-alkylcarbonyl, $C_1$–$C_4$-alkoxycarbonyl and $C_3$–$C_6$-cycloalkyl; is phenyl, phenyl-$C_1$–$C_4$-alkyl, phenylcarbonyl-$C_1$–$C_4$-alkyl, phenylcarbonyl, phenoxycarbonyl, heterocyclyl, heterocyclyl-$C_1$–$C_4$-alkyl, heterocyclylcarbonyl-$C_1$–$C_4$-alkyl, heterocyclyloxycarbonyl, where the phenyl or heterocyclyl radical of the radicals mentioned may be partially or fully halogenated and/or may carry one, two or three substituents selected from the group consisting of nitro, cyano, $C_1$–$C_4$-alkyl, $C_1$–$C_4$-haloalkyl, $C_1$–$C_4$-alkoxy and $C_1$–$C_4$-haloalkoxy.

Heterocyclyl is preferably a C-bonded 5-membered unsaturated ring or a C-bonded 6-membered unsaturated ring, in particular pyridin-2-yl or pyridin-3-yl.

Extraordinary preference is given to the compounds of the formula Ia1 (≡I where A=methanediyl, $R^3$, $R^7$–$R^{12}$=H; $R^6$=OH), in particular to the compounds Ia1.1 to Ia1.77 of Table 1, where the definitions of the radicals A and $R^1$ to $R^8$ are of particular importance for the compounds according to the invention not only in combination with one another but in each case also on their own.

TABLE 1

Ia1

| No. | $R^1$ | $R^2$ | $R^4$ | $R^5$ |
|---|---|---|---|---|
| Ia1.1 | Cl | $SO_2CH_3$ | H | H |
| Ia1.2 | Cl | $SO_2CH_3$ | $CH_3$ | H |
| Ia1.3 | Cl | $SO_2CH_3$ | $CH_3$ | $CH_3$ |
| Ia1.4 | Cl | $SO_2CH_3$ | $CH_2CH_3$ | H |
| Ia1.5 | Cl | $SO_2CH_3$ | $CH_2Cl$ | H |
| Ia1.6 | Cl | $SO_2CH_3$ | $CH_2F$ | H |
| Ia1.7 | Cl | $SO_2CH_3$ | $CH_2Br$ | H |
| Ia1.8 | Cl | $SO_2CH_3$ | $CF_3$ | H |
| Ia1.9 | Cl | $SO_2CH_3$ | $CHClCH_3$ | H |
| Ia1.10 | Cl | $SO_2CH_3$ | $CHFCH_3$ | H |
| Ia1.11 | Cl | $SO_2CH_3$ | $CH_2$ | |
| Ia1.12 | $CH_3$ | $SO_2CH_3$ | H | H |
| Ia1.13 | $CH_3$ | $SO_2CH_3$ | $CH_3$ | H |
| Ia1.14 | $CH_3$ | $SO_2CH_3$ | $CH_3$ | $CH_3$ |
| Ia1.15 | $CH_3$ | $SO_2CH_3$ | $CH_2CH_3$ | H |
| Ia1.16 | $CH_3$ | $SO_2CH_3$ | $CH_2Cl$ | H |
| Ia1.17 | $CH_3$ | $SO_2CH_3$ | $CH_2F$ | H |
| Ia1.18 | $CH_3$ | $SO_2CH_3$ | $CH_2Br$ | H |
| Ia1.19 | $CH_3$ | $SO_2CH_3$ | $CF_3$ | H |
| Ia1.20 | $CH_3$ | $SO_2CH_3$ | $CHClCH_3$ | H |
| Ia1.21 | $CH_3$ | $SO_2CH_3$ | $CHFCH_3$ | H |
| Ia1.22 | $CH_3$ | $SO_2CH_3$ | $CH_2$ | |
| Ia1.23 | Cl | $CF_3$ | H | H |
| Ia1.24 | Cl | $CF_3$ | $CH_3$ | H |
| Ia1.25 | Cl | $CF_3$ | $CH_3$ | $CH_3$ |
| Ia1.26 | Cl | $CF_3$ | $CH_2CH_3$ | H |
| Ia1.27 | Cl | $CF_3$ | $CH_2Cl$ | H |
| Ia1.28 | Cl | $CF_3$ | $CH_2F$ | H |
| Ia1.29 | Cl | $CF_3$ | $CH_2Br$ | H |
| Ia1.30 | Cl | $CF_3$ | $CF_3$ | H |
| Ia1.31 | Cl | $CF_3$ | $CHClCH_3$ | H |

TABLE 1-continued

Ia1

| No. | $R^1$ | $R^2$ | $R^4$ | $R^5$ |
|---|---|---|---|---|
| Ia1.32 | Cl | $CF_3$ | $CHFCH_3$ | H |
| Ia1.33 | Cl | $CF_3$ | $CH_2$ | |
| Ia1.34 | $CH_3$ | $CF_3$ | H | H |
| Ia1.35 | $CH_3$ | $CF_3$ | $CH_3$ | H |
| Ia1.36 | $CH_3$ | $CF_3$ | $CH_3$ | $CH_3$ |
| Ia1.37 | $CH_3$ | $CF_3$ | $CH_2CH_3$ | H |
| Ia1.38 | $CH_3$ | $CF_3$ | $CH_2Cl$ | H |
| Ia1.39 | $CH_3$ | $CF_3$ | $CH_2F$ | H |
| Ia1.40 | $CH_3$ | $CF_3$ | $CH_2Br$ | H |
| Ia1.41 | $CH_3$ | $CF_3$ | $CF_3$ | H |
| Ia1.42 | $CH_3$ | $CF_3$ | $CHClCH_3$ | H |
| Ia1.43 | $CH_3$ | $CF_3$ | $CHFCH_3$ | H |
| Ia1.44 | $CH_3$ | $CF_3$ | $CH_2$ | |
| Ia1.45 | $CH_2CH_3$ | $SO_2CH_3$ | H | H |
| Ia1.46 | $CH_2CH_3$ | $SO_2CH_3$ | $CH_3$ | H |
| Ia1.47 | $CH_2CH_3$ | $SO_2CH_3$ | $CH_3$ | $CH_3$ |
| Ia1.48 | $CH_2CH_3$ | $SO_2CH_3$ | $CH_2CH_3$ | H |
| Ia1.49 | $CH_2CH_3$ | $SO_2CH_3$ | $CH_2Cl$ | H |
| Ia1.50 | $CH_2CH_3$ | $SO_2CH_3$ | $CH_2F$ | H |
| Ia1.51 | $CH_2CH_3$ | $SO_2CH_3$ | $CH_2Br$ | H |
| Ia1.52 | $CH_2CH_3$ | $SO_2CH_3$ | $CF_3$ | H |
| Ia1.53 | $CH_2CH_3$ | $SO_2CH_3$ | $CHClCH_3$ | H |
| Ia1.54 | $CH_2CH_3$ | $SO_2CH_3$ | $CHFCH_3$ | H |
| Ia1.55 | $CH_2CH_3$ | $SO_2CH_3$ | $CH_2$ | |
| Ia1.56 | $CH_3$ | $SO_2CH_2CH_3$ | H | H |
| Ia1.57 | $CH_3$ | $SO_2CH_2CH_3$ | $CH_3$ | H |
| Ia1.58 | $CH_3$ | $SO_2CH_2CH_3$ | $CH_3$ | $CH_3$ |
| Ia1.59 | $CH_3$ | $SO_2CH_2CH_3$ | $CH_2CH_3$ | H |
| Ia1.60 | $CH_3$ | $SO_2CH_2CH_3$ | $CH_2Cl$ | H |
| Ia1.61 | $CH_3$ | $SO_2CH_2CH_3$ | $CH_2F$ | H |
| Ia1.62 | $CH_3$ | $SO_2CH_2CH_3$ | $CH_2Br$ | H |
| Ia1.63 | $CH_3$ | $SO_2CH_2CH_3$ | $CF_3$ | H |
| Ia1.64 | $CH_3$ | $SO_2CH_2CH_3$ | $CHClCH_3$ | H |
| Ia1.65 | $CH_3$ | $SO_2CH_2CH_3$ | $CHFCH_3$ | H |
| Ia1.66 | $CH_3$ | $SO_2CH_2CH_3$ | $CH_2$ | |
| Ia1.67 | Cl | $SO_2CH_2CH_3$ | H | H |
| Ia1.68 | Cl | $SO_2CH_2CH_3$ | $CH_3$ | H |
| Ia1.69 | Cl | $SO_2CH_2CH_3$ | $CH_3$ | $CH_3$ |
| Ia1.70 | Cl | $SO_2CH_2CH_3$ | $CH_2CH_3$ | H |
| Ia1.71 | Cl | $SO_2CH_2CH_3$ | $CH_2Cl$ | H |
| Ia1.72 | Cl | $SO_2CH_2CH_3$ | $CH_2F$ | H |
| Ia1.73 | Cl | $SO_2CH_2CH_3$ | $CH_2Br$ | H |
| Ia1.74 | Cl | $SO_2CH_2CH_3$ | $CF_3$ | H |
| Ia1.75 | Cl | $SO_2CH_2CH_3$ | $CHClCH_3$ | H |
| Ia1.76 | Cl | $SO_2CH_2CH_3$ | $CHFCH_3$ | H |
| Ia1.77 | Cl | $SO_2CH_2CH_3$ | $CH_2$ | |

Extraordinary preference is also given to the compounds of the formula Ia2, in particular to the compounds Ia2.1 to Ia2.77 which differ from the corresponding compounds Ia1.1 to Ia1.77 in that $R^9$ is methyl.

Ia2

Extraordinary preference is also given to the compounds of the formula Ia3, in particular to the compounds Ia3.1 to Ia3.77, which differ from the corresponding compounds Ia1.1 to Ia1.77 in that $R^9$ and $R^{10}$ are methyl.

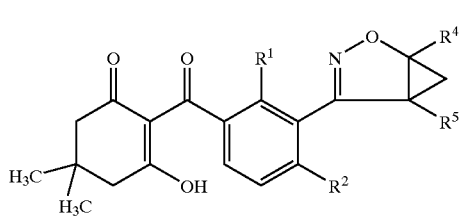

Ia3

Extraordinary preference is also given to the compounds of the formula Ia4, in particular to the compounds Ia4.1 to Ia4.77, which differ from the corresponding compounds Ia1.1 to Ia1.77 in that $R^7$ and $R^{11}$ are methyl.

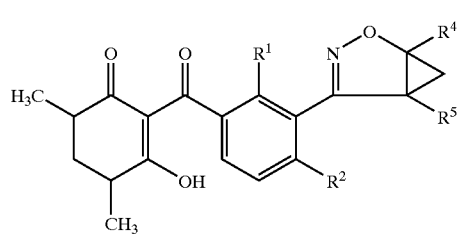

Ia4

Extraordinary preference is also given to the compounds of the formula Ia5, in particular to the compounds Ia5.1 to Ia5.77, which differ from the corresponding compounds Ia1.1 to Ia1.77 in that $R^7$ is methylthio and $R^8$ is methyl.

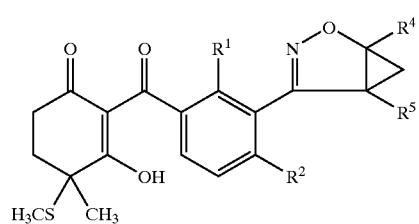

Ia5

Extraordinary preference is also given to the compounds of the formula Ia6, in particular to the compounds Ia6.1 to Ia6.77, which differ from the corresponding compounds Ia1.1 to Ia1.77 in that $R^7$ and $R^8$ together are pentane-1,5-diyl.

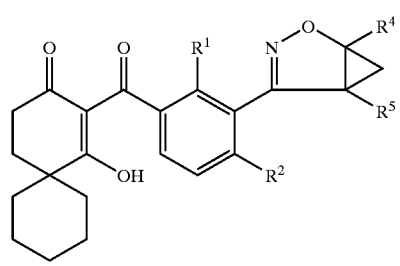

Ia6

Extraordinary preference is also given to the compounds of the formula Ia7, in particular to the compounds Ia7.1 to Ia7.77, which differ from the corresponding compounds Ia1.1 to Ia1.77 in that $R^8$ and $R^{12}$ together are ethane-1,2-diyl.

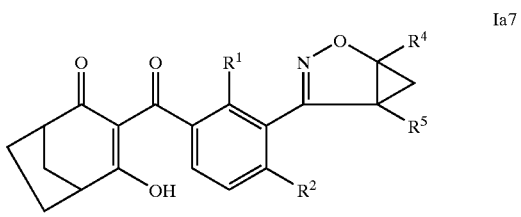

Ia7

Extraordinary preference is also given to the compounds of the formula Ia8, in particular to the compounds Ia8.1 to Ia8.77, which differ from the corresponding compounds Ia1.1 to Ia1.77 in that $R^7$, $R^8$, $R^{11}$ and $R^{12}$ are methyl and $R^9$ and $R^{10}$ together are an oxygen atom.

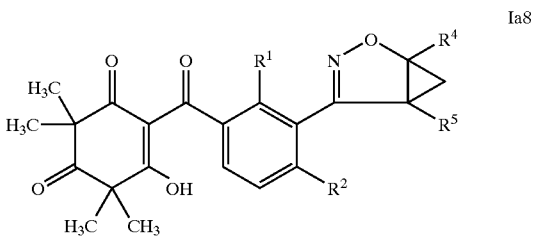

Ia8

Extraordinary preference is also given to the compounds of the formula Ia9, in particular to the compounds Ia9.1 to Ia9.77, which differ from the corresponding compounds Ia1.1 to Ia1.77 in that $R^9$ is hydroxyl.

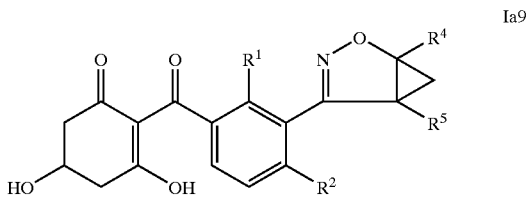

Ia9

3-(4,5-Dihydroisoxazol-3-yl)-substituted benzoylcyclohexenone derivatives of the formula I can be obtained by different routes, for example by the processes below:

Process A

Compounds of the formula I in which $R^6$ is OH are obtained, for example, by reacting compounds of the formula II with a benzoic acid derivative of the formula III, followed by rearrangement to benzoyl derivatives of the formula I:

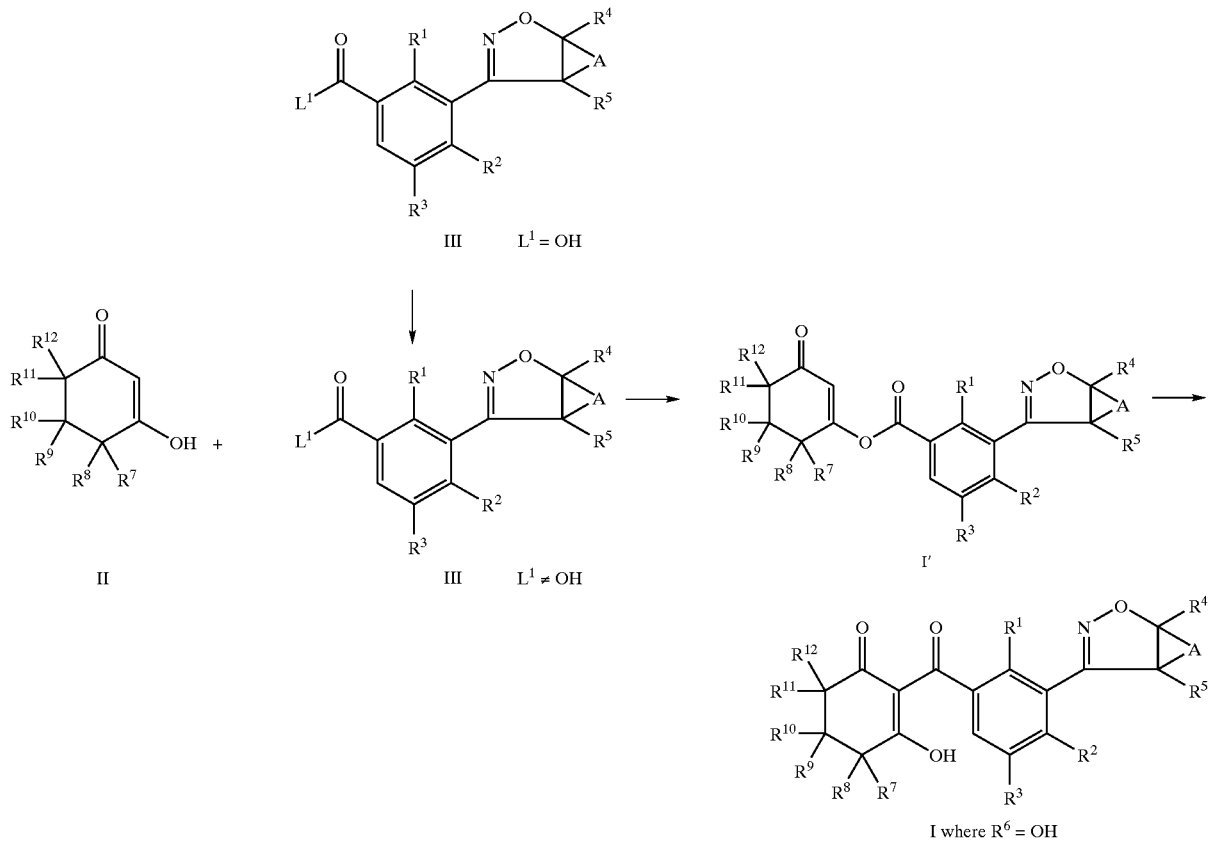

$L^1$ is hydroxyl or a nucleophilically displaceable leaving group, such as halogen, for example bromine or chlorine, hetaryl, for example imidazolyl or pyridyl, carboxylate, for example acetate, trifluoroacetate, etc.

An activated benzoic acid derivative III (where $L^1 \ne OH$) can be employed directly, such as in the case of the benzoyl halides, or be generated in situ, for example using dicyclohexylcarbodiimide, triphenylphosphine/ azodicarboxylic ester, 2pyridine disulfide/ triphenylphosphine, carbonyldiimidazole, etc.

It may be advantageous to carry out the acylation reaction in the presence of a base. The reactants and the auxiliary base are in this case advantageously employed in equimolar amounts. A slight excess of auxiliary base, for example from 1.2 to 1.5 molar equivalents, based on II, may be advantageous in certain cases.

Suitable auxiliary bases are tertiary alkylamines, pyridine or alkali metal carbonates. Suitable for use as solvents are, for example, chlorinated hydrocarbons, such as methylene chloride, 1,2dichloroethane, aromatic hydrocarbons, such as toluene, xylene, chlorobenzene, ethers, such as diethyl ether, methyl tert-butyl ether, dimethoxyethane, tetrahydrofuran, dioxane, polar aprotic solvents, such as acetonitrile, dimethylformamide, dimethyl sulfoxide, or esters, such as ethyl acetate or mixtures of these.

If the activated carboxylic acid component used is a benzoyl halide, it may be advantageous to cool the reaction mixture to 0–10° C. when adding this reaction partner. The mixture is subsequently stirred at 20–100° C., preferably at 25–50° C., until the reaction has ended. Work-up is carried out in a customary manner, for example by pouring the reaction mixture into water and extracting the product of value. Solvents which are particularly suitable for this purpose are methylene chloride, diethyl ether, dimethoxyethane and ethyl acetate. The organic phase is dried and the solvent is removed, after which the crude ester I' can be employed for the rearrangement without any further purification.

The rearrangement of the esters I' to the compounds of the formula I is advantageously carried out at 20–40° C. in a solvent and in the presence of a base and, if appropriate, using a cyano compound as catalyst.

Suitable solvents are, for example, acetonitrile, methylene chloride, 1,2-dichloroethane, dioxane, ethyl acetate, dimethoxyethane, tetrahydrofuran, toluene or mixtures of these. Preferred solvents are acetonitrile and dioxane.

Suitable bases are tertiary amines, such as triethylamine, pyridine or alkali metal carbonates, such as sodium carbonate or potassium carbonate, which are preferably employed in an equimolar amount or an up to four-fold excess, based on the ester. Preference is given to using triethylamine or alkali metal carbonates, preferably in twice the equimolar amount, based on the ester.

Suitable cyano compounds are inorganic cyanides, such as sodium cyanide and potassium cyanide, and organic cyano compounds, such as acetone cyanohydrin and trimethylsilyl cyanide. They are employed in an amount of from 1 to 50 mole percent, based on the ester. Preference is given to using acetone cyanohydrin or trimethylsilyl cyanide, for example in an amount of from 5 to 15, preferably 10, mole percent, based on the ester.

Work-up can be carried out in a manner known per se. The reaction mixture is, for example, acidified with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the resulting precipitate is filtered off with suction and/or extracted with methylene chloride or ethyl acetate, and the mixture is dried and concentrated. (Examples of cyanide-catalyzed rearrangement of enol esters of cyclohexane-1,3-diones are mentioned, for example, in EP-A 186 118 and U.S. Pat. No. 4,780,127).

The cyclohexenones of the formula II are known or can be prepared by processes known per se (for example EP-A 71 707, EP-A 142 741, EP-A 243 313, U.S. Pat No. 4,249,937, WO 92/13821).

The compounds of the formula III (where $L^1$=OH) can be obtained, for example, as follows:

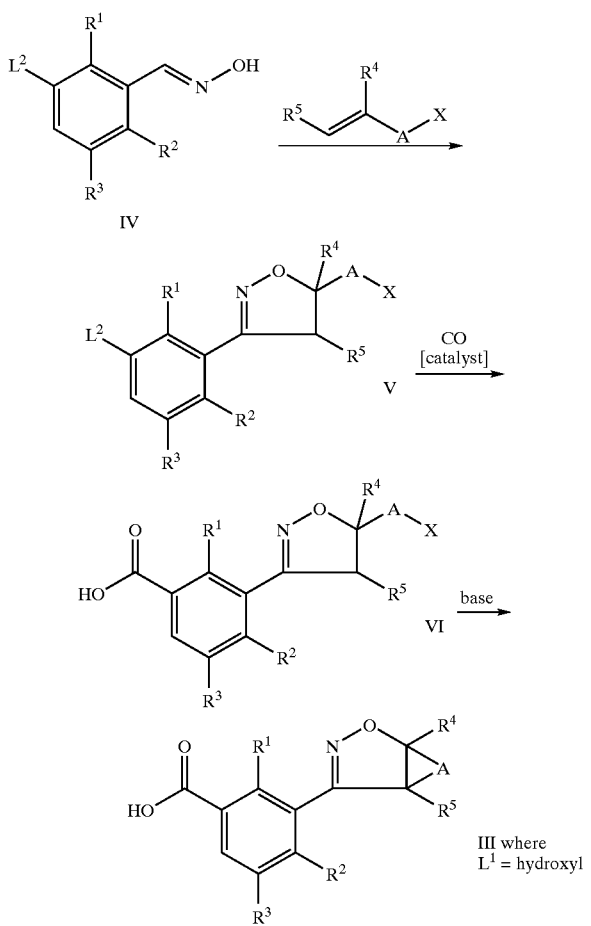

$L^2$ is a leaving group, such as halogen, for example chlorine, bromine or iodine, or sulfonate, such as mesylate or triflate; preference is given to bromine or triflate.

X is halogen, preferably chlorine or bromine.

The conversion of oximes of the formula IV into the 4,5-dihydroisoxazol-3-yl-benzene derivatives V can be carried out in a manner known per se, via the hydroxamic acid chloride intermediates. The latter are converted in situ into nitrile oxides which react with alkenes to form the desired products (cf., for example, Chem. Ber. 106 (1973), 3258–3274). Thus, the oxime IV is, for example, oxidized with sodium hypochlorite and reacted with an allyl halide, for example allyl chloride, in an inert solvent, such as methylene chloride, chloroform, tetrahydrofuran, diethyl ether, dioxane or acetonitrile, to give the 4,5-dihydroisoxazol-3-yl-benzene derivative V.

This is then reacted with carbon monoxide and water in the resence of a catalyst and of a base to give VI.

Suitable catalysts are palladium-ligand complexes in which the palladium is present in oxidation state 0, metallic palladium, which has optionally been absorbed on a support, and preferably palladium(II) salts. The reaction with palladium(II) salts and metallic palladium is preferably carried out in the presence of complex ligands.

An example of a suitable palladium(0)-ligand complex is tetrakis(triphenylphosphine)palladium.

Metallic palladium is preferably absorbed on an inert support such as, for example, activated carbon, silica, alumina, barium sulfate or calcium carbonate. The reaction is preferably carried out in the presence of complex ligands such as, for example, triphenylphosphine.

Examples of suitable palladiumn(II) salts are palladium acetate and palladium chloride. The presence of complex ligands such as, for example, triphenylphosphine is preferred.

Suitable complex ligands for the palladium-ligand complexes, or in whose presence the reaction with metallic palladium or palladium(II) salts is preferably carried out, are tertiary phosphines whose structure is represented by the following formulae:

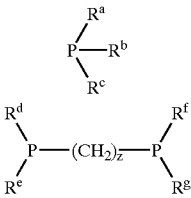

where z is 1 to 4 and the radicals $R^a$ to $R^g$ are $C_1$–$C_6$-alkyl, $C_3$–$C_6$-cycloalkyl, aryl-$C_1$–$C_2$-alkyl or, preferably, aryl. Aryl is, for example, naphthyl and unsubstituted or substituted phenyl such as, for example, 2-tolyl and, in particular, unsubstituted phenyl.

The complex palladium salts can be prepared in a manner known per se starting from commercially available palladium salts such as palladium chloride or palladium acetate and the appropriate phosphines, such as, for example, triphenylphosphine or 1,2-bis(diphenylphosphino)ethane. Many of the complexed palladium salts are also commercially available. Preferred palladium salts are [(R) (+)-2,2'-bis (diphenylphosphino)-1,1'-binaphthyl]-palladium(II) chloride, bis(triphenylphosphine)palladium(II) acetate and, in particular, bis(triphenylphosphine)palladium(II)chloride.

The palladium catalyst is usually employed in a concentration of from 0.05 to 5 mol %, and preferably 1 to 3 mol %.

Suitable bases are tertiary amines, such as, for example, N-methylpiperidine, ethyldiisopropylamine, 1,8-bisdimethylaminonaphthalene or, in particular triethylamine. Also suitable is alkali metal carbonate, such as sodium carbonate or potassium carbonate. However, mixtures of potassium carbonate and triethylamine are also suitable.

In general, from 2 to 4 molar equivalents, in particular 2 molar equivalents, of the alkali metal carbonate, and from 1 to 4 molar equivalents, in particular 2 molar equivalents, of the tertiary amine are employed, based on V.

Suitable solvents are nitrites, such as benzonitrile and acetonitrile, aromatic hydrocarbons, such as toluene, amides, such as dimethylformamide, dimethylacetamide, tetra–$C_1$–$C_4$-alkylureas or N-methylpyrrolidone and, preferably, ethers, such as tetrahydrofuran and methyl tert-butyl ether. Particularly preferred solvents are ethers, such as 1,4-dioxane and dimethoxyethane.

Ring closure of the compound VI to give the cyclopropane ring is carried out using strong bases, such as alkali metal alkoxides, for example potassium tert-butoxide, preferably in polar aprotic solvents, such as dimethyl sulfoxide.

Closure of the cyclopropane ring can also be carried out at the stage of the compound V, giving the compound VII which can be reacted further in a similar manner using carbon monoxide and water in the presence of a catalyst and base to give III where $L^1$=hydroxyl.

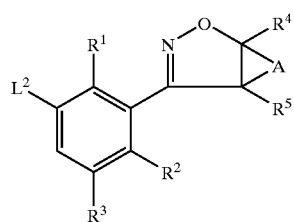
VII

It is also possible to obtain the compounds of the formula III where $L^1$=hydroxyl by converting an oxime of the formula VIII into the corresponding hydroxamic acid halide, in particular hydroxamic acid chloride, generating a nitrile oxide in situ and reacting this with an alkene (cf., for example, Chem. Ber. 106 (1973), 3258–3274). The ester is then hydrolyzed under conditions known per se, to give the compounds of the formula III where $L^1$=hydroxyl.

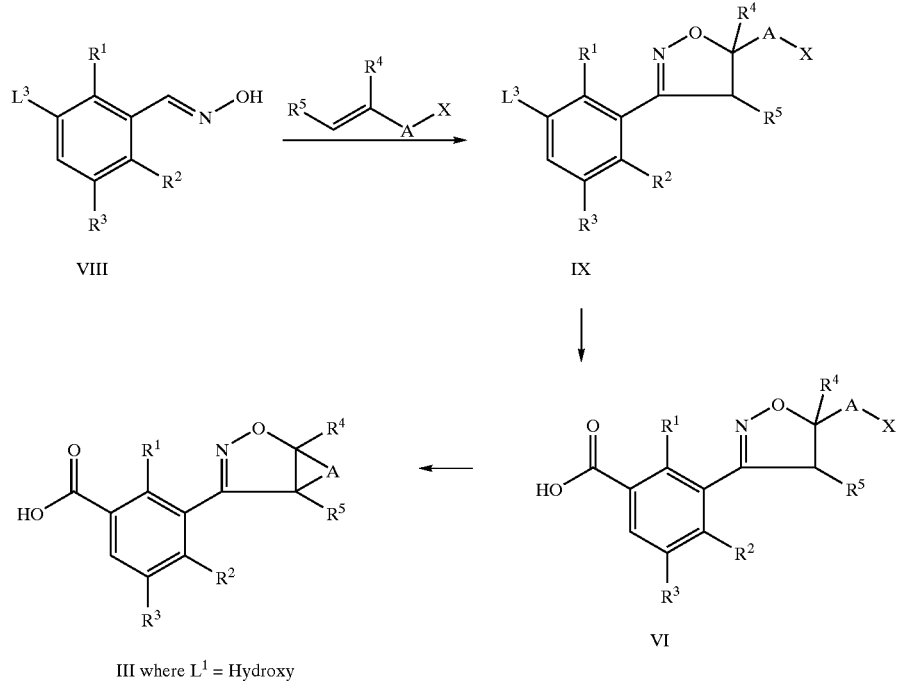

$L^3$ is a $C_1$–$C_6$-alkoxy radical and X is halogen, preferably chlorine or bromine.

Process B

Alternatively, the compounds of the formula I where $R^6$=OH can be prepared as follows:

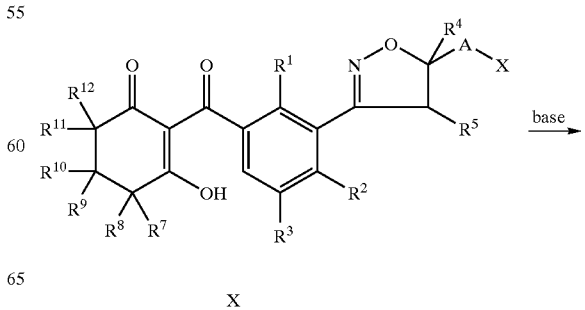

X

-continued

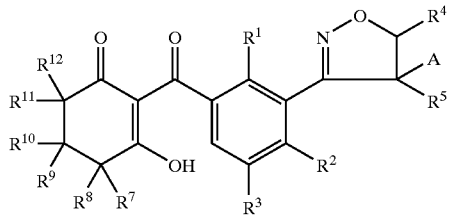

I where $R^6$ = OH

Suitable bases and solvents are those mentioned above for the ring closure.

Process C

Compounds of the formula I where $R^6$=$OR^{13}$ and $SR^{13}$ are obtained by reacting compounds of the formula I where $R^6$=hydroxyl and mercapto, respectively, with alkylating agents, carbamoylating agents or acylating agents $L^4$–$R^{13}$ (XI).

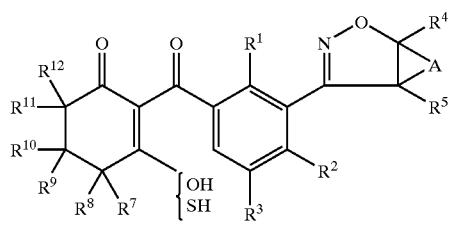

I where $R^6$ = OH, SH

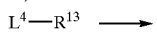

XI

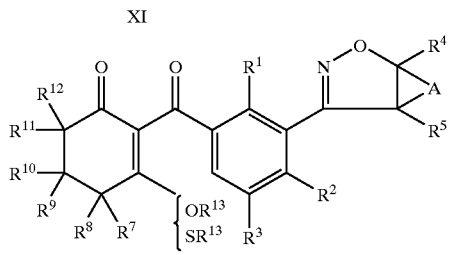

I where $R^6$ = $OR^{13}$, $SR^{13}$ $L^4$ is a nucleophilically displaceable leaving group, such as halogen, for example bromine or chlorine, acyloxy, for example acetyloxy or ethylcarbonyloxy, or alkylsulfonyloxy, for example methylsulfonyloxy or trifluoromethylsulfonyloxy;

The compounds of the formula XI can be employed directly, such as, for example, in the case of the carbonyl halides or carboxylic anhydrides, or be generated in situ (for example using dicyclohexylcarbodiimide, carbonyldiimidazole etc.).

The starting materials are generally employed in equimolar amounts. However, it may also be advantageous to employ an excess of one or the other component.

If appropriate, it may be advantageous to carry out the reaction in the presence of a base. The reactants and the auxiliary base are advantageously employed in aquimolar amounts. An excess of auxiliary base, for example from 1.5 to 3 molar equivalents, based on I (where $R^6$=OH), may be advantageous in certain cases.

Suitable auxiliary bases are tertiary alkylamines, such as triethylamine, aromatic amines, such as pyridine, alkali metal carbonates, for example sodium carbonate or potassium carbonate, alkali metal bicarbonates, such as sodium bicarbonate or potassium bicarbonate, alkali metal alkoxides, such as sodium methoxide, sodium ethoxide or potassium tert-butoxide, or alkali metal hydrides, for example sodium hydride. Preference is given to using triethylamine and pyridine.

Suitable solvents are, for example, chlorinated hydrocarbons, such as methylene chloride and 1,2-dichloroethane, aromatic hydrocarbons, for example toluene, xylene, chlorobenzene, ethers, such as diethyl ether, methyl tertbutyl ether, tetrahydrofuran and dioxane, polar aprotic solvents, such as acetonitrile and dimethylformamide, dimethyl sulfoxide, or esters, such as ethyl acetate, or mixtures of these.

In general, the reaction temperature is in the range from 0° C. to the boiling point of the reaction mixture.

The carbamoylating agent used can also be an isocyanate of the formula O=C=$NR^{13a}$, where $R^{13a}$ is $C_1$–$C_6$-alkyl, $C_3$–$C_6$-alkenyl or $C_3$–$C_6$-alkynyl.

Workup can be carried out in a manner known per se to give the product.

Process D

Compounds of the formula I where $R^6$=halogen are obtained by reacting compounds of the formula I where $R^6$=hydroxyl with a halogenating agent (Hal denotes halogen).

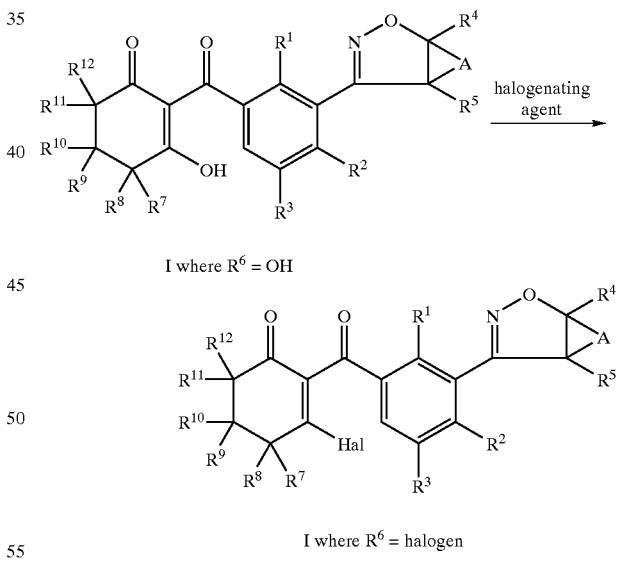

I where $R^6$ = halogen

Suitable halogenating agents are, for example, phosgene, diphosgene, triphosgene, thionyl chloride, oxalyl chloride, phosphorus oxychloride, phosphorus pentachloride, mesyl chloride, chloromethylene-N,N-dimethylammonium chloride, oxalyl bromide, phosphorus oxybromide, etc.

The starting materials are generally employed in equimolar amounts. It may also be advantageous to employ an excess of one or the other component.

Suitable solvents are, for example, chlorinated hydrocarbons, such as methylene chloride or 1,2- dichloroethane, aromatic hydrocarbons, for example toluene, xylene or chlorobenzene, polar aprotic solvents, such as acetonitrile, dimethylformamide or dimethyl sulfoxide, or mixtures of these. It is also possible to carry out the reaction without using a solvent.

In general, the reaction temperature is in the range from 0° C. to the boiling point of the reaction mixture.

Workup can be carried out in a manner known per se to give the product.

Process E

Compounds of the formula I where $R^6$=mercapto, $OR^{13}$ or $SR^{13}$ can furthermore be obtained by reacting compounds of the formula I where $R^6$=halogen with compounds of the formula XII, if appropriate in the presence of a base or with prior salt formation.

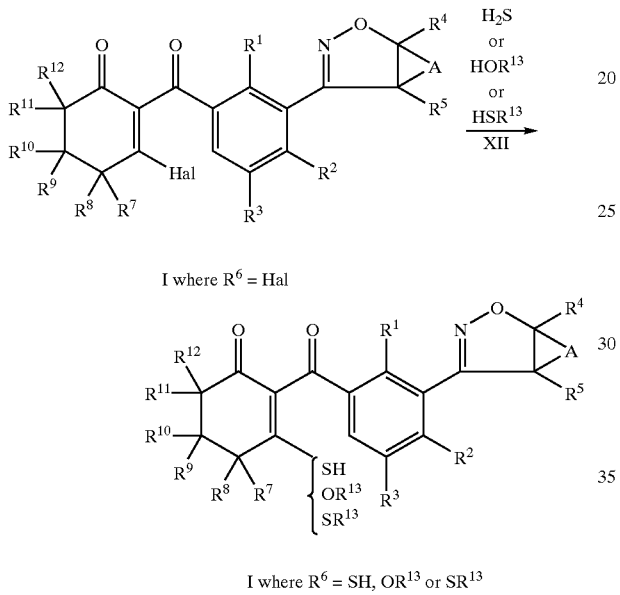

I where $R^6$ = Hal

I where $R^6$ = SH, $OR^{13}$ or $SR^{13}$

The starting materials are generally employed in equimolar amounts. However, it may also be advantageous to employ an excess of one or the other component.

If appropriate, it may also be advantageous to carry out the reaction in the presence of a base. The reactants and the base are advantageously employed in equimolar amounts. An excess of base, for example from 1.5 to 3 molar equivalents, based on I where $R^6$=Hal, may be advantageous in certain cases.

Suitable bases are tertiary alkylamines, such as triethylamine, aromatic amines, such as pyridine, alkali metal carbonates, for example sodium carbonate or potassium carbonate, alkali metal bicarbonates, such as sodium bicarbonate or potassium bicarbonate, alkali metal alkoxides, such as sodium methoxide, sodium ethoxide or potassium tert-butoxide or alkali metal hydrides, such as, for example, sodium hydride. Preference is given to using sodium hydride or potassium tert-butoxide.

Suitable solvents are, for example, chlorinated hydrocarbons, such as methylene chloride and 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or mixtures of these.

In general, the reaction temperature is in the range from 0° C. to the boiling point of the reaction mixture.

Workup can be carried out in a manner known per se to give the product.

Process F

It is furthermore possible to obtain compounds of the formula I where $R^6$=$SOR^{14}$ or $SO_2R^{14}$ by reacting the compounds of the formula I where $R^6$=$S^{14}$ with an oxidizing agent.

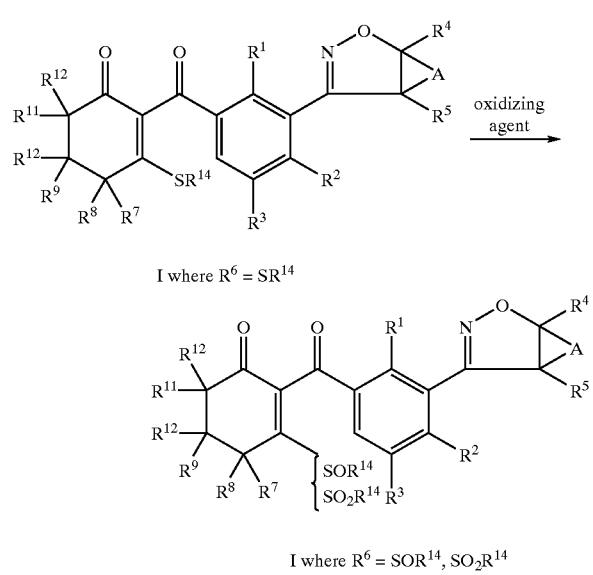

I where $R^6$ = $SR^{14}$

I where $R^6$ = $SOR^{14}$, $SO_2R^{14}$

Suitable oxidizing agents are, for example, m-chloroperbenzoic acid, peroxyacetic acid, trifluoroperoxyacetic acid, hydrogen peroxide, if appropriate in the presence of a catalyst, such as tungstate.

The starting materials are generally employed in equimolar amounts. It may be advantageous to employ an excess of one or the other component.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile or dimethylformamide, or esters, such as ethyl acetate, or mixtures of these.

In general, the reaction temperature is in the range from 0° C. to the boiling point of the reaction mixture.

Workup can be carried out in a manner known per se to give the product.

PREPARATION EXAMPLES

2-[2-Methyl-3-(2-oxa-3-azabicyclo[3.1.0]hex-3-en-4-yl)-4-methyl sulfonylbenzoyl]-1-hydroxy-4,6-dimethylcyclohex-1-en-3-one (compound 2.3)

At room temperature, 0.27 g (2.4 mmol) of potassium tert-butoxide is added to a solution of 0.36 g (0.8 mmol) of 2-[2-methyl-3-(5-chloromethyl-4,5-dihydroisoxazol-3-yl)-4-methyl sulfonylbenzoyl]-1-hydroxy-4,6-dimethylcyclohex-1-en-3-one in 4 ml of dimethyl sulfoxide, and the mixture was stirred for 12 hours. The reaction mixture was then introduced into 300 ml of 3% strength hydrochloric acid. Following extraction with ethyl acetate, the combined organic phases were washed with water and dried, and the solvent was removed. This gave 0.21 g (63% of theory) of the title compound of melting point 90–96° C. $^1$H-NMR (δ in ppm): δ=1.0–1.6 (m, 10H), 2.18 (s, 3H), 2.4–2.5 (m, 2H), 2.77 (m, 1H), 3.20 (s, 3H), 5.18 (s, 1H), 7.31 (d, 1H), 8.02 (d, 1H).

Compounds of the formula I which were prepared or are preparable in a similar manner are listed in Table 2.

vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N.rustica), Olea europaea, Oryza sativa, Phaseolus lunatus, Phaseolus vulgaris, Picea abies, Pinus spec., Pisum sativum, Prunus avium, Prunus persica, Pyrus communis, Ribes sylvestre, Ricinus communis, Saccharum officinarum, Secale cereale, Solanum tuberosum,

TABLE 2

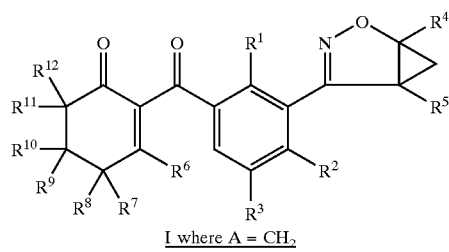

I where A = CH$_2$

| No. | R$^1$ | R$^2$ | R$^3$ | R$^4$ | R$^5$ | R$^6$ | R$^7$ | R$^8$ | R$^9$ | R$^{10}$ | R$^{11}$ | R$^{12}$ | physical data m.p. [° C.] |
|---|---|---|---|---|---|---|---|---|---|---|---|---|---|
| 2.1 | CH$_3$ | SO$_2$CH$_3$ | H | H | H | OH | H | H | CH$_3$ | CH$_3$ | H | H | 102 |
| 2.2 | CH$_3$ | SO$_2$CH$_3$ | H | H | H | OH | H | 1) | H | H | H | 1) | 121–128 |
| 2.3 | CH$_3$ | SO$_2$CH$_3$ | H | H | H | OH | CH$_3$ | H | H | H | CH$_3$ | H | 90–96 |
| 2.4 | CH$_3$ | SO$_2$CH$_3$ | H | H | H | OH | CH$_3$ | CH$_3$ | | =O | CH$_3$ | CH$_3$ | 88–94 |
| 2.5 | CH$_3$ | SO$_2$CH$_3$ | H | H | H | OH | CH$_3$S | CH$_3$ | H | H | H | H | 100–106 |
| 2.6 | CH$_3$ | SO$_2$CH$_3$ | H | H | H | OH | —(CH$_2$)$_5$— | | H | H | H | H | 84–90 |
| 2.7 | Cl | SO$_2$CH$_3$ | H | H | H | OH | H | H | CH$_3$ | CH$_3$ | H | H | 101–105 |
| 2.8 | CH$_3$ | SO$_2$CH$_3$ | H | CH$_3$ | H | OH | H | H | CH$_3$ | CH$_3$ | H | H | 112–120 |
| 2.9 | CH$_3$ | SO$_2$CH$_3$ | H | CH$_3$ | H | OH | CH$_3$ | CH$_3$ | | =O | CH$_3$ | CH$_3$ | 106–114 |
| 2.10 | CH$_3$ | SO$_2$CH$_3$ | H | H | CH$_3$ | OH | H | 1) | H | H | H | 1) | 112–118 |
| 2.11 | CH$_3$ | SO$_2$CH$_3$ | H | CH$_3$ | H | OH | H | 1) | H | H | H | 1) | 170–176 |
| 2.12 | CH$_3$ | SO$_2$CH$_3$ | H | CH$_3$ | H | OH | CH$_3$ | H | H | H | CH$_3$ | H | 98–112 |
| 2.13 | CH$_3$ | SO$_2$CH$_3$ | H | H | CH$_3$ | OH | H | H | CH$_3$ | CH$_3$ | H | H | 120–127 |
| 2.14 | CH$_3$ | SO$_2$CH$_3$ | H | CH$_3$ | H | OH | CH$_3$ | CH$_3$ | H | H | H | H | 120–130 |

1) R$^8$ and R$^{12}$ together = —CH$_2$CH$_2$—

The 3-(4,5-dihydroisoxazol-3-yl)-substituted benzoylcyclohexenone derivatives of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and harmful grasses in crops such as wheat, rice, maize, soya and cotton without causing any significant damage to the crop plants. This effect is mainly observed at low rates of application.

Depending on the application method used, the compounds of the formula I or the herbicidal compositions comprising them can additionally be employed in a further number of crop plants for eliminating undesirable plants. Examples of suitable crops are the following:

Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria Sorghum bicolor (s. vulgare), Theobroma cacao, Trifolium pratense, Triticum aestivum, Triticum durum, Vicia faba, Vitis vinifera and Zea mays.

In addition, the compounds of the formula I may also be used in crops which tolerate the action of herbicides owing to breeding, including genetic engineering methods.

The compounds of the formula I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting or granules, by means of spraying, atomizing, dusting, broadcasting or watering. The use forms depend on the intended aims; in any case, they should ensure a very fine distribution of the active compounds according to the invention.

The herbicidal compositions comprise a herbicidally effective amount of at least one compound of the formula I or an agriculturally useful salt of I and auxiliaries customarily used for formulating crop protection agents.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the 3-(4,5-dihydroisoxazol-3-yl)-substituted benzoylcyclohexenone derivatives, either as such or dissolved in an oil or solvent, can be homogenized in water by means of a wetting agent, tackifier, dispersant or emulsifier. Alternatively, it is also possible to prepare concentrates consisting of active substance, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl polyglycol ether or tributylphenyl polyglycol ether, alkylaryl polyether alcohols, isotridecyl alcohol, fatty alcohol ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or grinding the active substances together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise from about 0.001 to 98% by weight, preferably 0.01 to 95% by weight of at least one active compound. The active compounds are employed in a purity of from 90% to 100%, preferably from 95% to 100% (according to the NMR spectrum).

The production of such preparations is illustrated by the following formulation examples:

I. 20 parts by weight of the compound No. 2.1 are dissolved in a mixture consisting of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. 2.1 are dissolved in a mixture consisting of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. 2.1 are dissolved in a mixture consisting of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the active compound No. 2.1 are mixed thoroughly with 3 parts by weight of sodium diisobutylnaphthalenesulfonate, 17 parts by weight of the sodium salt of lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. 2.1 are mixed with 97 parts by weight of finely divided kaolin. This gives a dust which comprises 3% by weight of the active compound.

VI. 20 parts by weight of the active compound No. 2.1 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the active compound No. 2.1 is dissolved in a mixture consisting of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the active compound No. 2.1 is dissolved in a mixture of 80 parts by weight of cyclohexanone and 20 parts by weight of Wettol® EM 31 (=nonionic emulsifier based on ethoxylated castor oil). This gives a stable emulsion concentrate.

The compounds of the formula I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The application rates of the compound of the formula I are from 0.001 to 3.0, preferably from 0.01 to 1.0 kg/ha of active substance (a.s.), depending on the control target, the season, the target plants and the growth stage.

To widen the activity spectrum and to achieve synergistic effects, the 3-(4,5-dihydroisoxazol-3-yl)-substituted benzoylcyclohexenone derivatives of the formula I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-(hetaroyl/aroyl)-1,3-cyclohexanediones, hetarylaryl ketones, benzylisoxazolidinones, meta-CF$_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ether, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, priazolinones, triazolecarboxamides and uracils.

It may furthermore be advantageous to apply the compounds of the formula I, alone or else concomitantly in combination with other herbicides, or in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

Use Examples

The herbicidal activity of the 3-(4,5-dihydroisoxazol-3-yl)-substituted benzoylcyclohexenone derivatives of the formula I was demonstrated by the following greenhouse experiments:

The cultivation containers used were plastic flower pots containing loamy sand with approximately 3.0% of humus as the substrate. The seeds of the test plants were sown separately for each species.

For the pre-emergence treatment, directly after sowing the active compounds, which had been suspended or emulsified in water, were applied by means of finely distributing nozzles. The containers were irrigated gently to promote germination and growth and subsequently covered with transparent plastic hoods until the plants had rooted. This cover caused uniform germination of the test plants, unless this was adversely affected by the active compounds.

For the post-emergence treatment, the test plants were first grown to a height of from 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment. The application rate for the post-emergence treatment was 0.25 or 0.125 kg of a.s. (active substance)/ha.

Depending on the species, the plants were kept at 10–25° C. or 20–35° C. The test period extended over 2 to 4 weeks. During this time, the plants were tended, and their response to the individual treatments was evaluated.

The evaluation was carried out using a scale from 0 to 100. 100 means no emergence of the plants, or complete destruction of at least the aerial parts and 0 means no damage, or normal course of growth.

The plants used in the greenhouse experiments were of the following species:

| Scientific name | Deutscher Name | Common name |
| --- | --- | --- |
| Abutilon theophrasti | Chinesischer Hanf | velvet leaf |
| Avena fatua | Flughafer | wild oat |
| Brachiaria plantaginea | | alexandergrass |
| Chenopodium album | Weißer Gänsefuß | lamb's-quarters |
| Echinochloa crus galli | Hühnerhirse | barnyardgrass |
| Polygonum persicaria | Flohknöterich | lady's-thumb |

At application rates of 0.25 or 0.125 kg/ha, the compound No. 2.1 (Table 2) showed very good post-emergence action against the abovementioned undesirable plants.

We claim:

1. A 3-(4,5-dihydroisoxazol-3-yl)-substituted benzoylcyclohexenone derivative of the formula I

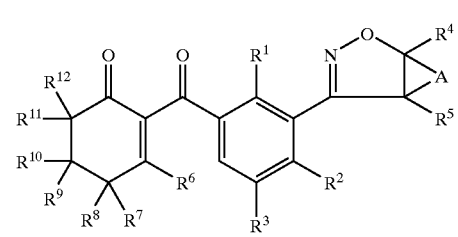

in which
A is $C_1$–$C_4$-alkanediyl which may carry one, two or three substituents selected from the group consisting of halogen and $C_1$–$C_4$-alkyl;
$R^1$ is $C_1$–$C_6$-alkyl, $C_1$–$C_6$-haloalkyl, $C_1$–$C_6$-alkoxy, $C_1$–$C_6$-haloalkoxy, halogen or nitro;
$R^2$ is $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, cyano, halogen or nitro;
$R^3$ is hydrogen, $C_1$–$C_6$-alkyl or halogen;
$R^4$, $R^5$ independently of one another are hydrogen, $C_1$–$C_4$-alkyl or $C_1$–$C_4$-haloalkyl; or
$R^4$, $R^5$ together are $C_1$–$C_4$-alkanediyl which may carry one, two or three substituents selected from the group consisting of halogen and $C_1$–$C_4$-alkyl;
$R^6$ is hydroxyl, mercapto, halogen, $OR^{13}$, $SR^{13}$, $SOR^{14}$ or $SO_2R^{14}$;

R⁷, R¹¹ independently of one another are hydrogen, $C_1$–$C_4$-alkyl, $C_1$–$C_4$-alkylthio or $C_1$–$C_4$-alkoxycarbonyl;

R⁸, R¹⁰, R¹² independently of one another are hydrogen or $C_1$–$C_4$-alkyl;

R⁹ is hydrogen, hydroxyl, halogen, $C_1$–$C_6$-alkyl, $C_1$–$C_6$-haloalkyl, di($C_1$–$C_6$-alkoxy)methyl, ($C_1$–$C_6$-alkoxy)($C_1$–$C_6$-alkylthio)methyl, di($C_1$–$C_6$-alkylthio)methyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkoxycarbonyl, $C_1$–$C_6$-haloalkoxycarbonyl; 1,3-dioxolan-2-yl, 1,3-dioxan-2-yl, 1,3-oxathiolan-2-yl, 1,3-dithiolan-2-yl or 1,3-dithian-2-yl, where the six last-mentioned radicals may carry one, two or three substituents selected from $C_1$–$C_4$-alkyl; or R⁷ and R⁸ or R¹¹ and R¹² together are $C_1$–$C_5$-alkanediyl which may carry one, two or three substituents selected from the group consisting of halogen, cyano, $C_1$–$C_4$-alkyl, $C_1$–$C_4$-haloalkyl and $C_1$–$C_4$-alkoxycarbonyl; or R⁷ and R⁸ or R¹¹ and R¹² together are $C_1$–$C_5$-alkanediyl which may carry one, two or three substituents selected from the group consisiting of halogen, cyano, $C_1$–$C_4$-alkyl, $C_1$–$C_4$-haloalkyl and $C_1$–$C_4$-alkoxycarbonyl; or R⁸ and R⁹ or R⁹ and R¹² together are a chemical bond or $C_1$–$C_5$-alkanediyl which may carry one, two or three substituents selected from the group consisting of halogen, cyano, $C_1$–$C_4$-alkyl, $C_1$–$C_4$-haloalkyl and $C_1$–$C_4$-alkoxycarbonyl; or R⁸ and R¹² together are $C_1$–$C_4$-alkanediyl which may carry one, two or three substituents selected from the group consisting of halogen, cyano, $C_1$–$C_4$-alkyl, $C_1$–$C_4$-alkoxycarbonyl; or R⁹ and R¹⁰ together are —O—(CH$_2$)$_p$—O—, —O—(CH$_2$)$_p$—S—, —S—(CH$_2$)$_p$—S—, —O—(CH$_2$)$_q$— or —S—(CH$_2$)$_q$— which may carry one, two or three substituents selected from the group consisting of halogen, cyano, $C_1$–$C_4$-alkyl, $C_1$–$C_4$-haloalkyl and $C_1$–$C_4$-alkoxycarbonyl; or R⁹ and R¹⁰ together are an oxygen atom;

R¹³ is $C_1$–$C_6$-alkyl, $C_3$–$C_6$-alkenyl, $C_3$–$C_6$-haloalkenyl, $C_3$–$C_6$-alkynyl, $C_3$–$C_6$-cycloalkyl, $C_1$–$C_{20}$-alkylcarbonyl, $C_2$–$C_{20}$-alkenylcarbonyl, $C_2$–$C_6$-alkynylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N,N-di($C_1$–$C_6$-alkyl)aminothiocarbonyl, $C_1$–$C_6$-alkoxyimino-$C_1$–$C_6$-alkyl, where the alkyl, alkoxy and cycloalkyl radicals mentioned may be partially or fully halogenated and/or may carry one, two or three substituents selected from the group consisting of cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, $C_1$–$C_4$-alkylaminocarbonyl or $C_3$–$C_6$-cycloalkyl; is phenyl, phenyl-$C_1$–$C_6$-alkyl, phenylcarbonyl-$C_1$–$C_6$-alkyl, phenylcarbonyl, phenoxycarbonyl, phenoxythiocarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl, where the phenyl or heterocyclyl radical of the radicals mentioned may be partially or fully halogenated and/or may carry one, two or three substituents selected from the group consisting of nitro, cyano, $C_1$–$C_4$-alkyl, $C_1$–$C_4$-haloalkyl, $C_1$–$C_4$-alkoxy and $C_1$–$C_4$-haloalkoxy;

R¹⁴ is $C_1$–$C_6$-alkyl, $C_3$–$C_6$-alkenyl, $C_3$–$C_6$-haloalkenyl, $C_3$–$C_6$-alkynyl or $C_3$–$C_6$-cycloalkyl, where the alkyl and cycloalkyl radicals mentioned may be partially or fully halogenated and/or may carry one, two or three substituents selected from the group consisting of cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, $C_1$–$C_4$-alkylaminocarbonyl, N,N-di($C_1$–$C_4$-alkyl)aminocarbonyl or $C_3$–$C_6$-cycloalkyl; is phenyl, phenyl-$C_1$–$C_6$-alkyl, phenylcarbonyl-$C_1$–$C_6$-alkyl, heterocyclyl, heterocyclyl-$C_1$–$C_6$-alkyl or heterocyclylcarbonyl-$C_1$–$C_6$-alkyl, where the phenyl or heterocyclyl radical of the radicals mentioned may be partially or fully halogenated and/or may carry one, two or three substituents selected the group consisting of nitro, cyano, $C_1$–$C_4$-alkyl, $C_1$–$C_4$-haloalkyl, $C_1$–$C_4$-alkoxy and $C_1$–$C_4$-haloalkoxy;

p is 2, 3 or 4;

q is 1, 2, 3, 4 or 5;

and its agriculturally useful salts.

2. A 3-(4,5-dihydroisoxazol-3-yl)-substituted benzoylcyclohexenone derivative as claimed in claim 1 in which A is methanediyl.

3. A 3-(4,5-dihydroisoxazol-3-yl)-substituted benzoylcyclohexenone derivative as claimed in claim 1, in which R¹ is $C_1$–$C_4$-alkyl or halogen;

R² is $C_1$–$C_4$-haloalkyl, $C_1$–$C_4$-alkylsulfonyl or halogen;

R³ is hydrogen,

R⁴ is hydrogen, $C_1$–$C_4$-alkyl or $C_1$–$C_4$-haloalkyl;

R⁵ is hydrogen or $C_1$–$C_4$-alkyl.

4. A 3-(4,5-dihydroisoxazol-3-yl)-substituted benzoylcyclohexenone derivative as claimed in claim 1 in which R⁷ and R¹¹ independently of one another are hydrogen, $C_1$–$C_4$-alkyl or $C_1$–$C_4$-alkylthio;

R⁸, R¹⁰, R¹² independently of one another are hydrogen or methyl and

R⁹ is hydrogen, hydroxyl, $C_1$–$C_6$-alkyl or di($C_1$–$C_6$-alkoxy)methyl;

R⁷ and R⁸ or R⁸ and R⁹ or R⁹ and R¹² or R⁸ and R¹² or R¹¹ and R¹² together are $C_1$–$C_5$-alkanediyl which may carry one, two or three substituents selected from the group consisting of halogen, cyano, $C_1$–$C_4$-alkyl, $C_1$–$C_4$-haloalkyl and $C_1$–$C_4$-alkoxycarbonyl; or R⁹ and R¹⁰ together are an oxygen atom.

5. A 3-(4,5-dihydroisoxazol-3-yl)-substituted benzoylcyclohexenone derivative as claimed in claim 1 in which R⁶ is hydroxyl, OR¹³ or SR¹³; and R¹³ is $C_1$–$C_6$-alkyl, $C_1$–$C_{20}$-alkylcarbonyl, $C_1$–$C_6$-alkoxycarbonyl, $C_1$–$C_6$-alkylthiocarbonyl, where the alkyl and alkoxy radicals may be partially or fully halogenated and/or may carry one, two or three substituents selected from the group consisting of cyano, $C_1$–$C_4$-alkoxy, $C_1$–$C_4$-alkylthio, $C_1$–$C_4$-alkylcarbonyl, $C_1$–$C_4$-alkoxycarbonyl and $C_3$–$C_6$-cycloalkyl; is phenyl, phenyl-$C_1$–$C_4$-alkyl, phenylcarbonyl-$C_1$–$C_4$-alkyl, phenylcarbonyl, phenoxycarbonyl, heterocyclyl, heterocyclyl-$C_1$–$C_4$-alkyl, heterocyclylcarbonyl- $C_1$–$C_4$-alkyl, heterocyclyloxycarbonyl, where the phenyl or heterocyclyl radical of the radicals mentioned may be partially or fully halogenated and/or may carry one, two or three substituents selected from the group consisting of nitro, cyano, $C_1$–$C_4$-alkyl, $C_1$–$C_4$-haloalkyl, $C_1$–$C_4$-alkoxy or $C_1$–$C_4$-haloalkoxy.

6. A process for preparing 3-(4,5-dihydroisoxazol-3-yl)-substituted benzoylcyclohexenone derivatives of the formula I where $R^6$=OH as claimed in claim 1, which comprises acylating a cyclohexenone of the formula II

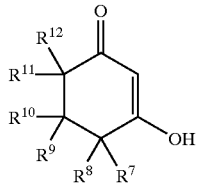

with a benzoic acid derivative of the formula III

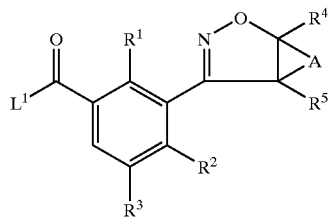

in which the variables A, $R^1$ to $R^5$ and $R^7$ to $R^{12}$ are as defined in claim 1 and $L^1$ is hydroxyl or a nucleophilically displaceable leaving group and rearranging the acylation product to a compound of the formula I in which $R^6$ is hydroxyl.

7. A process for preparing 3-(4,5-dihydroisoxazol-3-yl)-substituted benzoylcyclohexenone derivatives of the formula I where $R^6$=OH as claimed in claim 1, which comprises reacting a compound of the formula X,

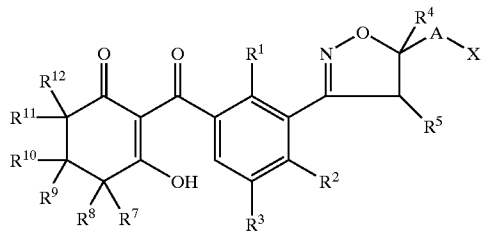

in which A, $R^1$ to $R^5$ and $R^7$ to $R^{12}$ are as defined in claim 1 and X is halogen with a base to give a compound of the formula I where $R^6$=OH.

8. A process for preparing compounds of the formula I where $R^6$=$OR^{13}$ or $SR^{13}$ as claimed in claim 1, which comprises reacting a compound of the formula I where $R^6$=OH or SH,

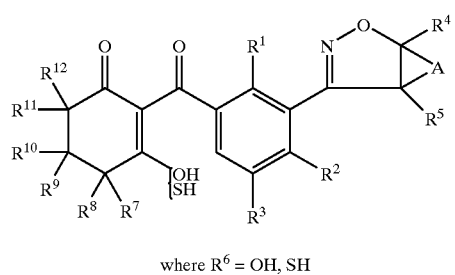

where $R^6$ = OH, SH in which A, $R^1$ to $R^5$ and $R^7$ to $R^{12}$ are as defined in claim 1 with a compound of the formula XI,

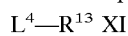

$L^4$—$R^{13}$ XI where the variable $R^{13}$ is as defined in claim 1 and $L^4$ is a nucleophilically displaceable leaving group.

9. A process for preparing compounds of the formula I where $R^6$=halogen as claimed in claim 1, which comprises reacting a compound of the formula I where $R^6$=OH,

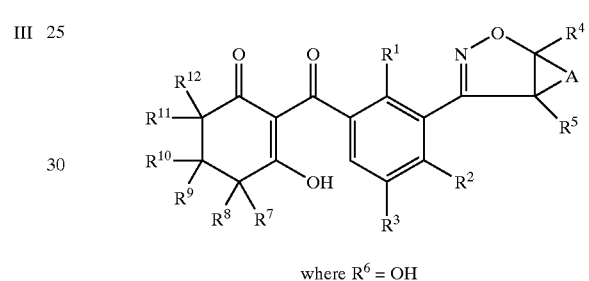

where $R^6$ = OH where the variables A, $R^1$ to $R^5$ and $R^7$ to $R^{12}$ are as defined in claim 1 with a halogenating agent.

10. A process for preparing compounds of the formula I where $R^6$=mercapto, $OR^{13}$ or $SR^{13}$ as claimed in claim 1, which comprises reacting a compound of the formula I where $R^6$=halogen,

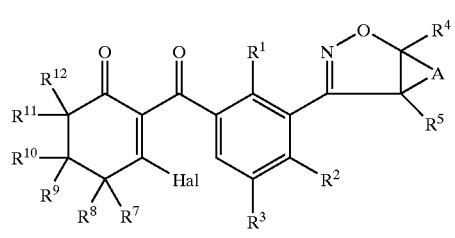

where $R^6$ = Hal in which the variables A, $R^1$ to $R^5$ and $R^7$ to $R^{12}$ are as defined in claim 1 with a compound of the formula XII,

$H_2S$ or $HOR^{13}$ or $HSR^{13}$ XII where $R^{13}$ is as defined in claim 1, optionally in the presence of a base.

11. A process for preparing compounds of the formula I where $R^6$=$SOR^{14}$ or $SO_2R^{14}$ as claimed in claim 1, which comprises reacting a compound of the formula I where $R^6$=$SR^{14}$,

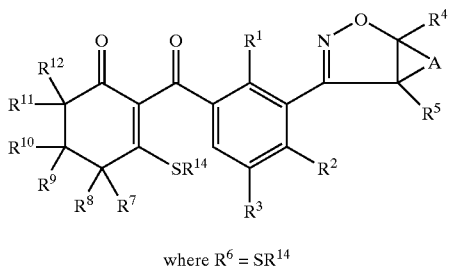

where $R^6 = SR^{14}$ where the variables A, $R^1$ to $R^5$, $R^7$ to $R^{12}$ and $R^{14}$ are as defined in claim 1 with an oxidizing agent.

12. A composition, comprising a herbicidally effective amount of at least one 3-(4,5-dihydroisoxazol-3-yl)-substituted benzoylcyclohexenone derivative of the formula I or an agriculturally useful salt thereof as claimed in claim 1 and auxiliaries customarily used for formulating crop protection agents.

13. A method for controlling undesirable vegetation, which comprises allowing a herbicidally effective amount of at least one 3-(4,5-dihydroisoxazol-3-yl)-substituted benzoylcyclohexenone derivative of the formula I or an agriculturally useful salt thereof as claimed in claim 1, to act on plants, their habitat and/or on seeds.

14. A method of use of 3-(4,5-dihydroisoxazol-3-yl)-substituted benzoylcyclohexenone derivatives of the formula I or of agriculturally useful salts thereof as claimed in claim 1 as herbicides.

* * * * *

UNITED STATES PATENT AND TRADEMARK OFFICE
CERTIFICATE OF CORRECTION

PATENT NO. : 6,667,333 B2  
APPLICATION NO. : 10/130021  
DATED : December 23, 2003  
INVENTOR(S) : Kudis et al.

It is certified that error appears in the above-identified patent and that said Letters Patent is hereby corrected as shown below:

Col. 37, claim 1:

line 12, after "1,3-oxathiolan-2-yl," insert --1,3-oxathian-2-yl--;

omit the material on lines 20-24 as a duplicate of that on lines 16-19.

Col. 38, claim 1, line 22, after "selected" insert --from--.

Signed and Sealed this

Nineteenth Day of February, 2008

JON W. DUDAS  
*Director of the United States Patent and Trademark Office*